(12) United States Patent
Dorman

(10) Patent No.: US 8,066,730 B2
(45) Date of Patent: Nov. 29, 2011

(54) MEDICAL DILATOR SYSTEM OR DILATOR DEVICE

(75) Inventor: John Dorman, Midland, TX (US)

(73) Assignee: Scapa Flow, LLC, Midland, TX (US)

( * ) Notice: Subject to any disclaimer, the term of this patent is extended or adjusted under 35 U.S.C. 154(b) by 823 days.

(21) Appl. No.: 11/598,986

(22) Filed: Nov. 14, 2006

(65) Prior Publication Data

US 2007/0129747 A1    Jun. 7, 2007

Related U.S. Application Data

(60) Provisional application No. 60/736,661, filed on Nov. 14, 2005.

(51) Int. Cl.
*A61M 29/00* (2006.01)

(52) U.S. Cl. .......................................... 606/191

(58) Field of Classification Search .............. 606/190, 606/191, 197, 199; 604/104, 117, 164.01; 600/184
See application file for complete search history.

(56) References Cited

U.S. PATENT DOCUMENTS

| | | | |
|---|---|---|---|
| 609,909 A | 8/1898 | Seaman | |
| 719,487 A * | 2/1903 | Minor | 604/104 |
| 2,884,123 A | 4/1959 | Dann et al. | |
| 4,031,783 A | 6/1977 | Paul et al. | |
| D247,512 S | 3/1978 | Sandler | |
| D264,824 S | 6/1982 | Sandel | |
| 4,350,151 A | 9/1982 | Scott | |
| 4,449,532 A * | 5/1984 | Storz | 606/191 |
| 4,573,448 A * | 3/1986 | Kambin | 606/170 |
| D295,445 S | 4/1988 | Freeman | |
| 4,735,202 A | 4/1988 | Williams | |
| 4,772,266 A * | 9/1988 | Groshong | 604/164.05 |
| D300,561 S | 4/1989 | Asa et al. | |
| 4,862,891 A * | 9/1989 | Smith | 606/191 |
| 4,917,274 A | 4/1990 | Asa et al. | |
| D318,116 S | 7/1991 | Michelson | |
| 5,158,543 A * | 10/1992 | Lazarus | 604/164.1 |
| 5,279,567 A * | 1/1994 | Ciaglia et al. | 604/117 |
| D344,903 S | 3/1994 | Gampp, Jr. et al. | |
| D364,501 S | 11/1995 | Gough | |
| 5,472,426 A * | 12/1995 | Bonati et al. | 604/164.1 |
| 5,487,739 A * | 1/1996 | Aebischer et al. | 604/890.1 |

(Continued)

*Primary Examiner* — Elizabeth Houston
(74) *Attorney, Agent, or Firm* — Gardere Wynne Sewell LLP; Robert J. Ward

(57) ABSTRACT

A medical dilating system and method are provided that include a dilator device having an elongated shape with an exterior surface, a first end and a second end. The first end of the dilator device includes a tapered tip configured to penetrate and provide an opening in the tissue of a patient, and a plurality of sleeves cooperatively configured to widen the opening in the tissue. The dilator device includes an interior wall that generally defines an open interior volume extending from an opening of the second end of the dilator device to one or more openings in the tapered tip at the first end of the dilator device. Each of the plurality of sleeves has an elongated shape with an exterior surface, a first end, a second end, and an interior wall that generally defines an open interior volume substantially extending from an opening of the first end of the respective sleeve to the second end of the respective sleeve. The plurality of sleeves include at least a first sleeve operable to allow the internal wall of the first sleeve to be substantially positioned around the exterior surface of the dilator device, and a second sleeve operable to allow the internal wall of the second sleeve to be substantially positioned around the exterior surface of the first sleeve.

8 Claims, 3 Drawing Sheets

U.S. PATENT DOCUMENTS

| | | |
|---|---|---|
| D387,427 S | 12/1997 | Bucholz et al. |
| D393,715 S | 4/1998 | Strickland |
| 5,741,290 A | 4/1998 | Hsieh |
| 5,817,102 A | 10/1998 | Johnson et al. |
| 5,967,970 A * | 10/1999 | Cowan et al. ............... 600/207 |
| 5,976,146 A * | 11/1999 | Ogawa et al. ............. 606/86 R |
| 6,010,520 A * | 1/2000 | Pattison ...................... 606/191 |
| 6,425,859 B1 * | 7/2002 | Foley et al. ................. 600/204 |
| 6,776,765 B2 | 8/2004 | Soukup et al. |
| 6,916,330 B2 * | 7/2005 | Simonson .................... 606/191 |
| 6,969,373 B2 * | 11/2005 | Schwartz et al. ........ 604/170.03 |
| 6,981,664 B1 | 1/2006 | Fugere |
| D518,178 S | 3/2006 | Christiansen |
| D589,143 S | 3/2009 | Mauch |
| 7,666,188 B2 | 2/2010 | Anderson et al. |
| 2002/0123744 A1 | 9/2002 | Reynard |
| 2004/0122462 A1 * | 6/2004 | Bakos et al. ................. 606/191 |
| 2005/0070949 A1 * | 3/2005 | Bakos et al. ................. 606/191 |
| 2005/0256525 A1 * | 11/2005 | Culbert et al. ................. 606/53 |
| 2006/0004398 A1 * | 1/2006 | Binder et al. ................ 606/191 |
| 2007/0255208 A1 * | 11/2007 | McMichael et al. .......... 604/104 |
| 2008/0033280 A1 | 2/2008 | Lubock et al. |
| 2010/0094093 A1 | 4/2010 | Miles et al. |

* cited by examiner

MEDICAL DILATOR SYSTEM OR DILATOR DEVICE

CROSS REFERENCE TO RELATED APPLICATIONS

The present document claims the benefit of the earlier filing date of co-pending U.S. provisional patent application Ser. No. 60/736,661, entitled "MEDICAL DILATOR SYSTEM or dilator device," filed in the U.S. Patent and Trademark Office on Nov. 14, 2005, and having a common inventor as the present document, the entire contents of which is incorporated herein by reference.

BACKGROUND OF THE INVENTION

1. Field of the Invention

The present invention relates to medical devices and more particularly, relates to a medical device system for retraction of tissues and insertion of instruments in connection with surgeries.

2. Discussion of the Background

Surgery often requires making openings in a patient. Current techniques often use invasive techniques which result in trauma to the patient during the surgery of the patient. Therefore, there exists a need for minimally invasive system which reduces trauma during surgery.

SUMMARY OF THE INVENTION

Accordingly, one aspect of the present invention is to provide a medical dilating system includes a dilator device having an elongated shape with an exterior surface, a first end and a second end. The first end of the dilator device includes a tapered tip configured to penetrate and provide an opening in the tissue of a patient, and a plurality of sleeves cooperatively configured to widen the opening in the tissue. The dilator device includes an interior wall that generally defines an open interior volume extending from an opening of the second end of the dilator device to one or more openings in the tapered tip at the first end of the dilator device. Each of the plurality of sleeves has an elongated shape with an exterior surface, a first end, a second end, and an interior wall that generally defines an open interior volume substantially extending from an opening of the first end of the respective sleeve to the second end of the respective sleeve. The plurality of sleeves include at least a first sleeve operable to allow the internal wall of the first sleeve to be substantially positioned around the exterior surface of the dilator device, and a second sleeve operable to allow the internal wall of the second sleeve to be substantially positioned around the exterior surface of the first sleeve.

Another aspect of the present invention is to provide a medical dilating system for penetrating from the surface of a tissue to a desired depth in the tissue to provide an opening in the tissue for use in surgery. The medical dilating system includes a dilator device and a plurality of sleeves. The dilator device has an exterior surface and an elongated shape with a first end, a body, and a second end. The first end of the dilator device includes a tapered tip. The body includes depth indicators to assist a user in determining a depth of penetration of the dilator device into the tissue. The dilator device includes an interior wall that generally defines an open interior volume extending from an opening of the second end of the dilator device to one or more openings in the tapered tip at the first end of the dilator device. The plurality of sleeves each has an exterior surface, a first end, a second end, and an interior wall that generally defines an open interior volume extending from the first end of the respective sleeve to the second end of the respective sleeve. The plurality of sleeves include at least a first sleeve operable to allow the internal wall of the first sleeve to be substantially positioned around the exterior surface of the dilator device, and a second sleeve operable to allow the internal wall of the second sleeve to be substantially positioned around the exterior surface of the first sleeve.

Yet another aspect of the present invention is to provide a method for penetrating and providing an opening in the tissue of a patient using a dilating medical dilating system that includes a dilator device and a plurality of sleeves. The dilator device includes an exterior surface having one or more depth indicators, a tapered end configured to penetrate and provide the opening in the tissue of the patient, and a second end. The dilator device includes an interior wall that generally defines an open interior volume extending from an opening of the second end of the dilator device to one or more openings in the tapered tip at the first end of the dilator device. Each of the plurality of sleeves includes an elongated shape with an exterior surface having one or more depth indicators, a first end, a second end, and an interior wall that generally defines an open interior volume substantially extending from an opening of the first end of the respective sleeve to the second end of the respective sleeve. The method includes positioning the dilator device in the tissue of the patient, adjusting a depth of penetration of the dilator device in the tissue using the depth indicators of the dilator device, positioning the internal wall of a first one of the plurality of sleeves substantially around the external surface of the first one of the plurality of sleeves, and adjusting a depth of penetration of the first one of the plurality of sleeves in the tissue using the depth indicators of the first one of the plurality of sleeves.

BRIEF DESCRIPTION OF THE DRAWINGS

A more complete appreciation of the present invention and many of the attendant advantages thereof will be readily obtained as the sane becomes better understood by reference to the following detailed description when considered in conjunction with the accompanying drawings, wherein.

DETAILED DESCRIPTION OF THE PREFERRED EMBODIMENTS

Figure 1:
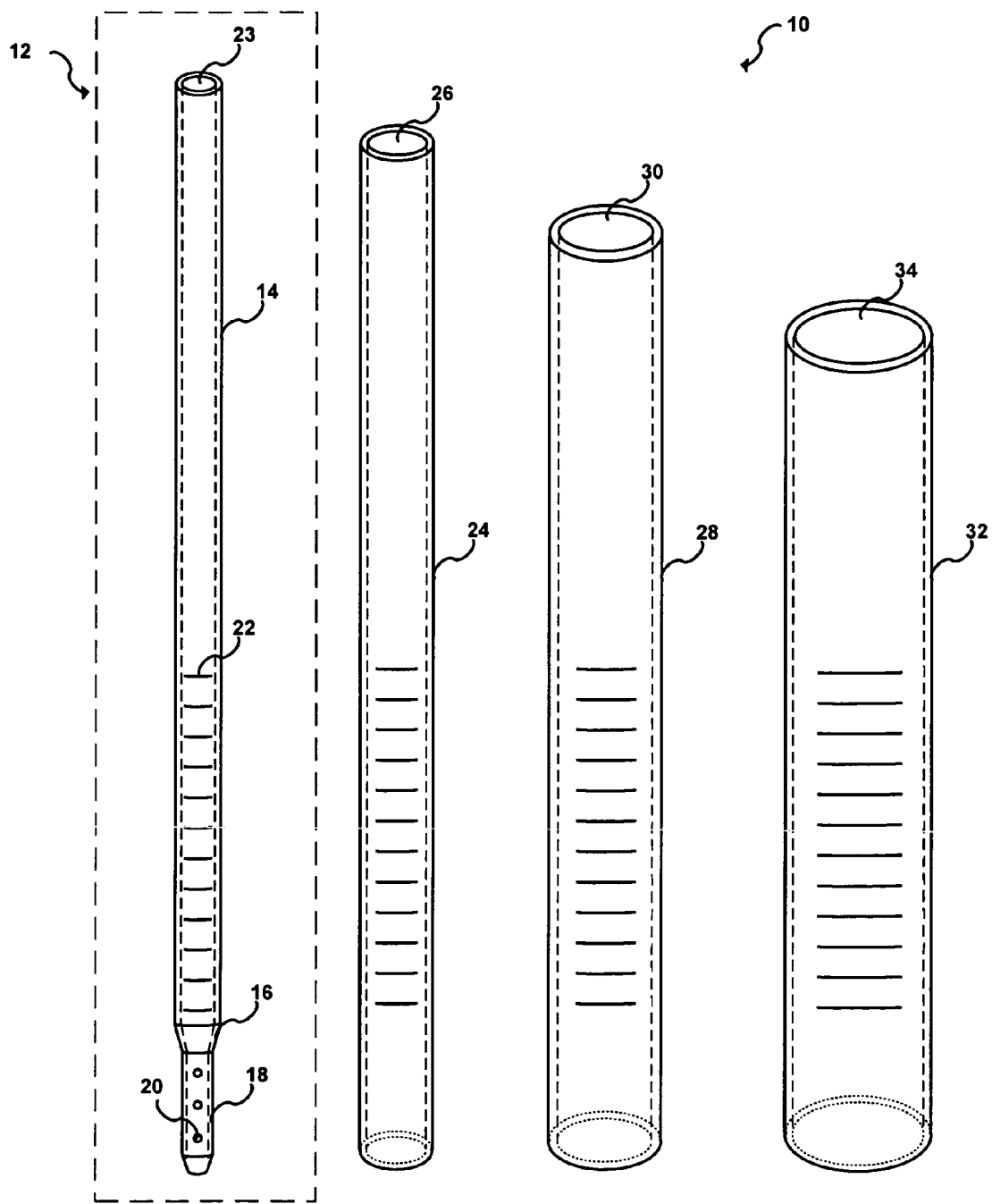
FIG. 1 is a block diagram illustrating a medical dilator system according to the present invention.

Referring now to the drawings, wherein like reference numerals designate identical or corresponding parts throughout the several views, preferred embodiments of the present invention are described.

The medical dilator system is designed to be used as a minimally invasive system (MIS) during the surgery of a patient. In operation, the medical dilator system is used to create and dilate an opening in the patient. For instance, the medical dilator system may be used, but is not limited to, microscopic and endoscopic surgeries.

Referring to FIG. 1, a block diagram illustrating a medical dilator system 10 is shown. The medical dilator system 10 includes a medical dilator 12, and one or more elongated sleeves 24, 28 and 32 of different sizes. Each elongated sleeve having openings on both ends and a hollow interior 26, 30 and 34 extending therethrough. The medical dilator 12 includes a elongated member 14 having a tapered end 18. The one or more elongated sleeves 24, 28 and 32 are each configured with hollow interiors 26, 30 and 34, each successively larger.

Figure 3:
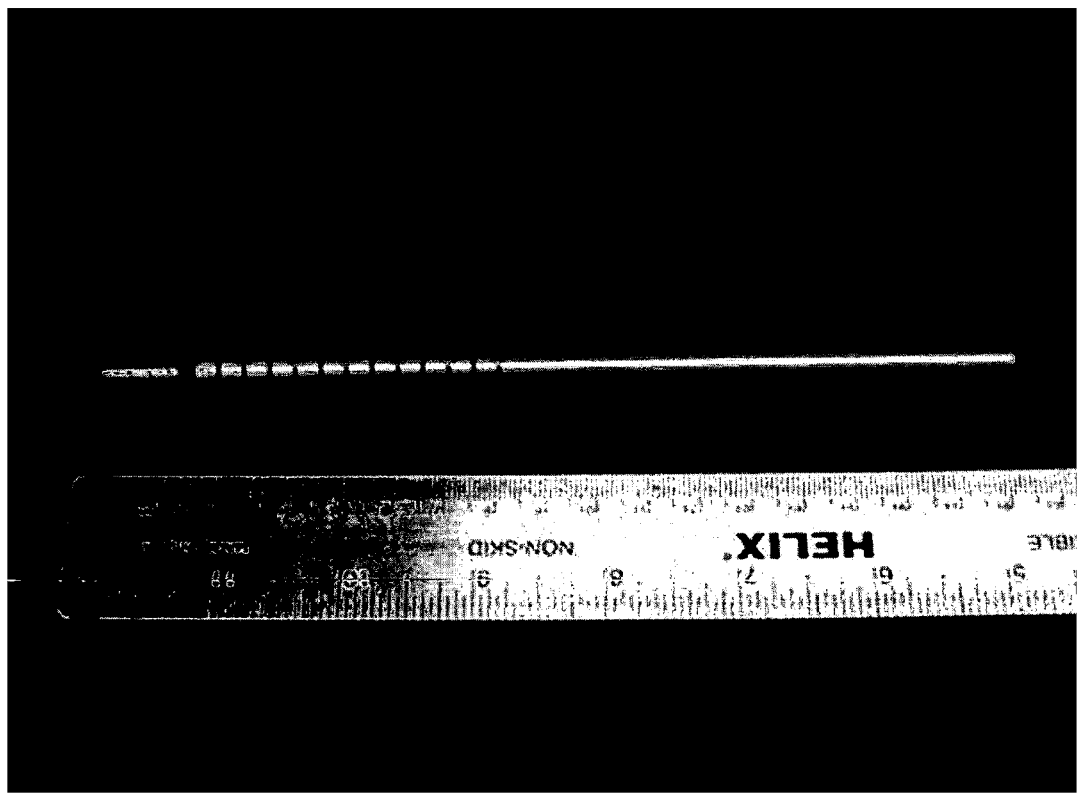
FIG. 3 is picture of a medical dilator device according to the present invention.

In one embodiment, a first sleeve 24 is configured such that it may be slid around the medical dilator 12, a second sleeve 28 may be slid around the first sleeve 24, and a third sleeve 32 may be slid around the second sleeve 28. This process is repeated with a fewer or greater number of sleeves until the desired dilation is achieved. This allows a small hole to be created through which a biopsy or resection can be performed. For instance, a hole of about 1 cm in diameter may be created. FIG. 3 further shows a picture of a medical dilator device 12 according to the present invention.

In one possible embodiment, the medical dilator 12 includes an opening at an end opposite the tapered end 18 and a hollow interior 23 extending through at a least a portion of the medical dilator 12 to one or more holes 20 extending along a portion of the tapered end. In this arrangement, the one or more holes 20 and the hollow interior 23 are configured such that fluid may flow through the holes 20 and hollow interior 23 and egress through the end of the medical dilator 12. Such fluids, including, but are not limited to, cerebrospinal fluid or cyst fluid, can egress through the end of the dilator 12.

Optionally, the medical dilator system includes one or more exterior depth markings 22 that indicate the deep that the dilator 12 has been placed within the patient 36. The depth markings 22 may be in any measurement unit, including, but not limited to, centimeters and inches.

Figure 2:
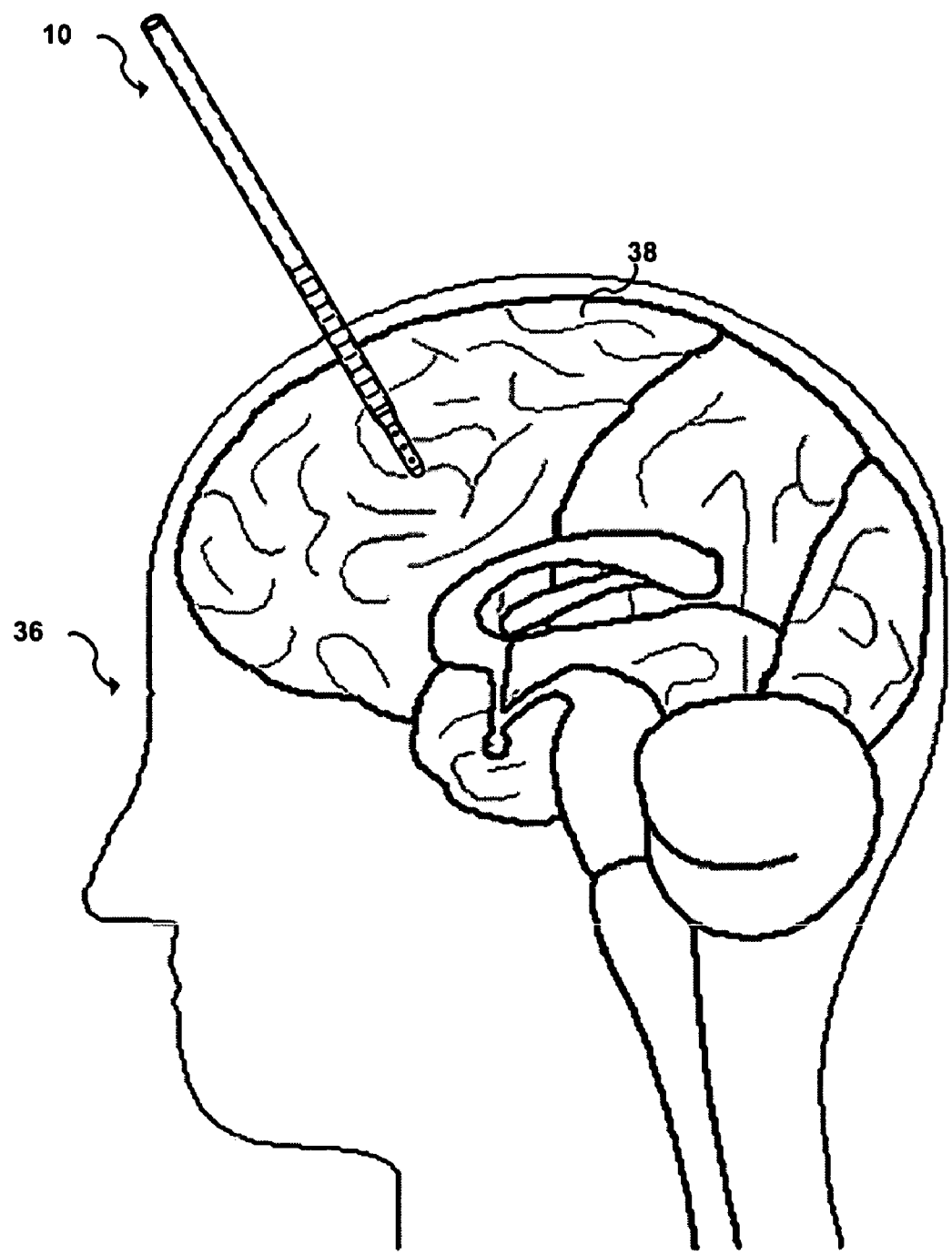
FIG. 2 is a block diagram illustrating a medical dilator placed through the cerebral of a patient according to an embodiment of the present invention.

Referring to FIG. 2, a block diagram illustrating a medical dilator 12 placed through the cerebral 38 of a patient 36 according to one possible embodiment of the present invention is shown. In this embodiment, the medical dilator 12 is slowly inserted into the cerebral 38 of the patient 36. Although the medical dilator 12 is shown placed through the cerebral 38 of a patient 36, it is not limited to such use and may be effectively used throughout the body of the patient 36 where a dilation is required. For example, in some embodiments, the medical dilator 12 may be positioned at or adjacent a tumor or lesion.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise then as specifically described.

The invention claimed is:

1. A method for penetrating and dilating an opening in a tissue of a brain of a patient using a dilating medical dilating system including a dilator device and a plurality of sleeves, wherein the dilator device includes an exterior surface having one or more depth indicators, a first end that is tapered and configured to penetrate and provide the opening in the tissue of the patient, and a second end, wherein the dilator device includes an interior wall that generally defines an open interior volume extending from an opening at the second end of the dilator device to one or more openings along a side portion of the tapered tip at the first end of the dilator device, wherein the dilator device is operable to allow a liquid to flow from one or more of the openings along the side portion of the tapered tip, through the open interior volume of the dilator device to the opening of the second end of the dilator device, and wherein each of the plurality of sleeves comprises an elongated shape with an exterior surface having one or more depth indicators, a first end, a second end, and an interior wall that generally defines an open interior volume substantially extending from an opening of the first end of the respective sleeve to the second end of the respective sleeve, the method comprising:

positioning the dilator device in the tissue of the patient;

adjusting a depth of penetration of the dilator device in the tissue using the depth indicators of the dilator device;

positioning the interior wall of a first one of the plurality of sleeves substantially around the exterior surface of the dilator device;

adjusting a depth of penetration of the first one of the plurality of sleeves in the tissue using the depth indicators of the first one of the plurality of sleeves; and allowing a liquid to flow from one or more of the openings along the side portion of the tapered tip of the dilator device, through the open interior volume of the dilator device to the opening of the second end of the dilator device.

2. The method of claim 1, further comprising:

positioning the interior wall of a second one of the plurality of sleeves substantially around the exterior surface of the first one of the plurality of sleeves; and adjusting a depth of penetration of the second one of the plurality of sleeves in the tissue using the depth indicators of the second one of the plurality of sleeves.

3. The method of claim 1, further comprising positioning the dilator device at or adjacent a tumor.

4. The method of claim 1, further comprising positioning the dilator device at or adjacent a lesion.

5. The method of claim 1, wherein the one or more depth indicators of the plurality of sleeves comprises measurements in centimeters.

6. The method of claim 1, wherein the one or more depth indicators of the plurality of sleeves comprises measurements in inches.

7. The method of claim 1, wherein the one or more depth indicators of the dilator device comprises measurements in centimeters.

8. The method of claim 1, wherein the one or more depth indicators of the dilator device comprises measurements in inches.

\* \* \* \* \*